United States Patent [19]
Clarke et al.

[11] Patent Number: 4,612,802
[45] Date of Patent: Sep. 23, 1986

[54] METHOD AND APPARATUS FOR RAPIDLY DETERMINING THE MOISTURE CONTENT OF A SUBSTANCE

[75] Inventors: Michael R. Clarke, West Vancouver; Gary E. Troughton, Vancouver, both of Canada

[73] Assignee: Forintek Canada Corp., Vancouver, Canada

[21] Appl. No.: 679,313

[22] Filed: Dec. 7, 1984

[30] Foreign Application Priority Data

Mar. 14, 1984 [CA] Canada ................................ 449578

[51] Int. Cl.⁴ ...................... G01N 19/10; G01N 21/86
[52] U.S. Cl. ........................................ 73/73; 374/45; 73/75
[58] Field of Search ................ 73/73, 75, 77, 337; 374/45

[56] References Cited
U.S. PATENT DOCUMENTS 3,216,241 11/1965 Hansen ................................. 73/75
3,350,789 11/1967 Davies ................................. 73/73

Primary Examiner—Charles Frankfort
Assistant Examiner—Denis E. Corr
Attorney, Agent, or Firm—Frishauf, Holtz, Goodman & Woodward

[57] ABSTRACT

A method and apparatus for rapidly determining the moisture content of a substance. An area of one surface only of the substance is subjected to a predetermined intensity of radiant energy for a selected period of time and the temperature rise is measured. The rise in the surface temperature of the substance such as pieces of wood, is approximately inversely proportional to the moisture content of the wood and thus is easily determined. This is obtainable by transporting the substance on a fixed speed conveyor past a heat source, variations in the rise and fall in the surface temperature readings immediately following the application of heat are representative of its moisture content; low readings indicating high moisture content while high readings being indicative of low moisture content.

17 Claims, 7 Drawing Figures

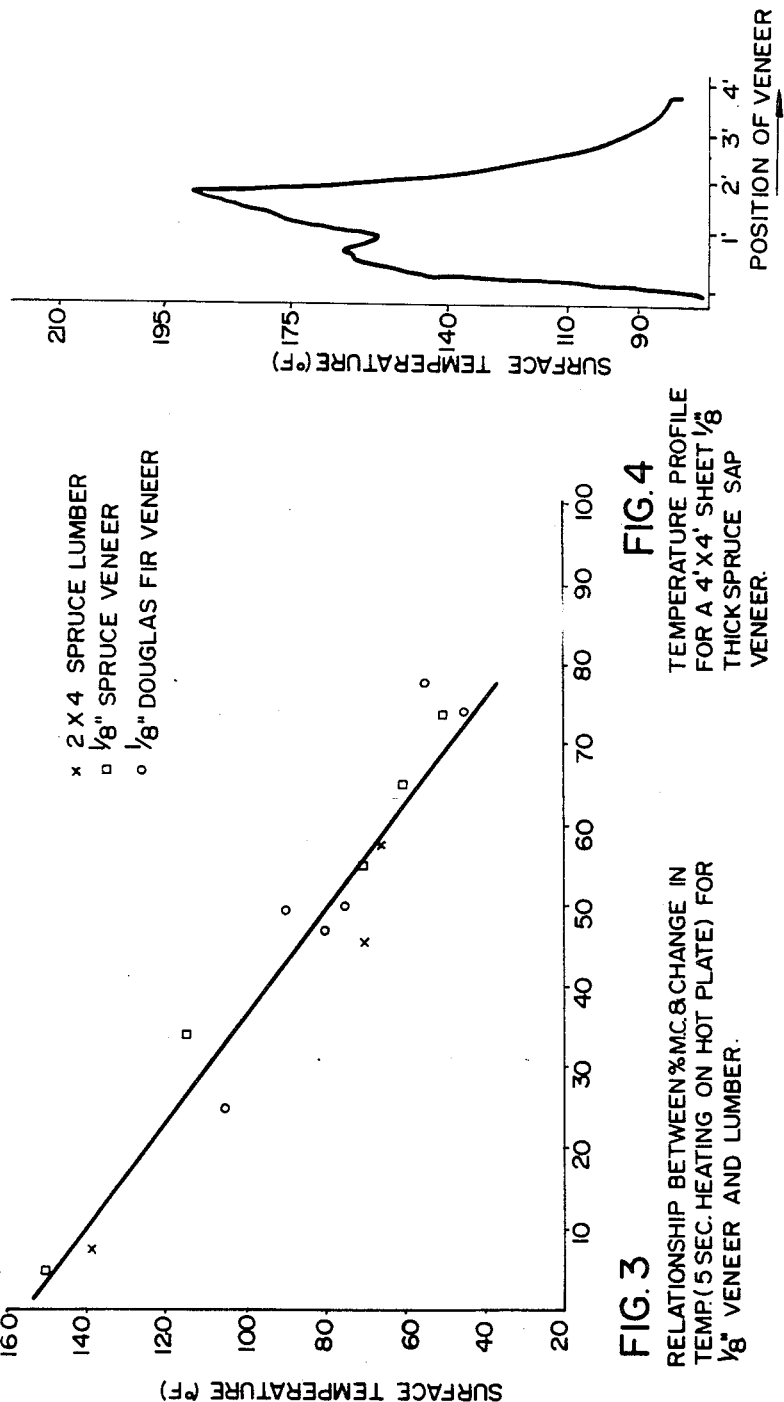
FIG. 3 RELATIONSHIP BETWEEN %M.C. & CHANGE IN TEMP.(5 SEC. HEATING ON HOT PLATE) FOR 1/8" VENEER AND LUMBER.
FIG. 4 TEMPERATURE PROFILE FOR A 4'X4' SHEET 1/8" THICK SPRUCE SAP VENEER.

GRAPH SHOWING THE RELATIONSHIP BETWEEN FINAL SURFACE TEMPERATURE & % MOISTURE CONTENT FOR UNSEASONED 1/8" SPRUCE SAP VEENER.

TEMPERATURE PROFILES FOR FOUR DIFFERENT POSITIONS IN UNSEASONED 2"X6" HEMLOCK LUMBER FOUR FEET IN LENGTH

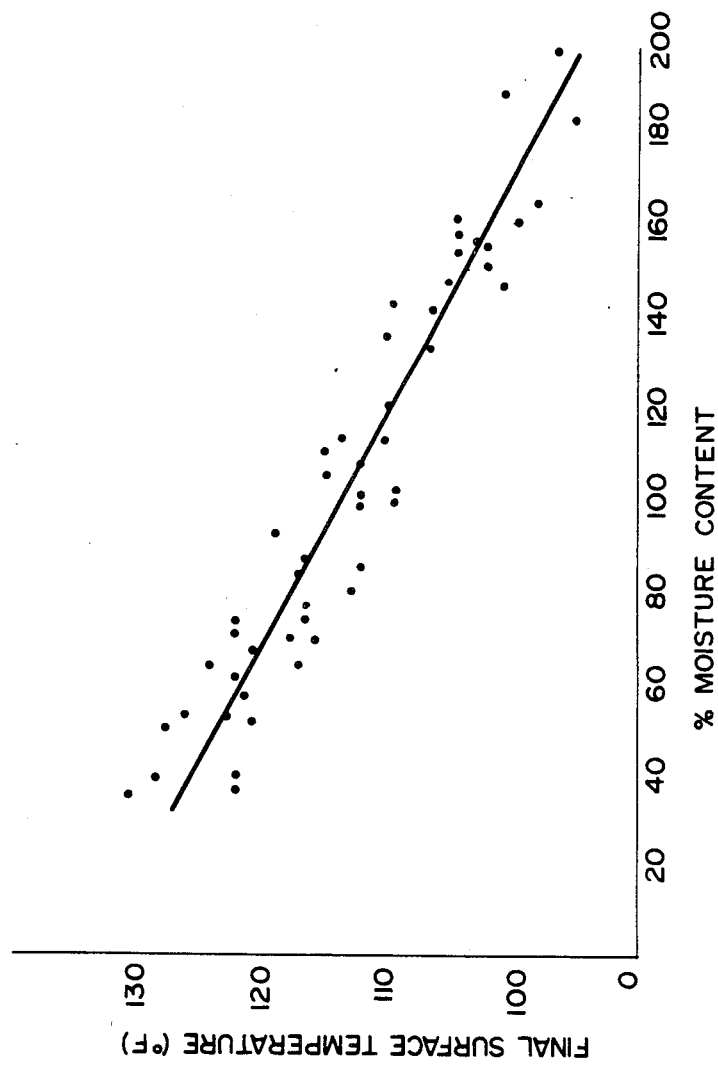

4,612,802

METHOD AND APPARATUS FOR RAPIDLY DETERMINING THE MOISTURE CONTENT OF A SUBSTANCE

FIELD OF INVENTION

This invention relates to an improved method and apparatus for rapidly determining the moisture content of a substance particularly fibrous products such as logs, wood pieces, lumber and the like. While the invention is disclosed with reference to wood products it is also applicable to other substances as will be seen hereafter.

BACKGROUND INVENTION

Hitherto, the commonest procedure used in determining the moisture content of a substance or material is to hold same at a temperature above the boiling point of water until such time as all of the water present has evaporated. The difference in the weight of the substance or material before and after heating, represent the weight of the water lost; from which the moisture content can be calculated. During this heating procedure, the temperature of the material being examined cannot exceed the boiling point of water, until all of the water is evaporated. Thus, although the heating capacity must be substantially greater than merely the heat required to evaporate the water from the substance being examined, the temperature which is utilized usefully, is only marginally above the boiling point of water. Accordingly, drying ovens used for moisture determinations commonly are set at 105 degrees Celcius (compared to the boiling point of water at 100 degrees Celcius).

Another major reason, necessitating a minimum temperature in drying materials of biological origin, are the changes which occur at elevated temperatures. For example, case hardening of a material effectively traps the water inside, making moisture determinations impossible. In these instances, it may be necessary to reduce the temperature at which water boils by applying vacuum to the material. In still other instances, where even these lower temperatures are unacceptable, sublimation of water from the frozen sample by vacuum techniques may be necessary (i.e., freeze-drying, as it is commonly called). Although all these procedures based on the transfer of heat are well known, and can be highly automated, they require extended periods of time, usually 24 hours or longer.

One method of determining the moisture content of a material is disclosed in Canadian Pat. No. 729,885 issued Mar. 15, 1966 to Crown Zellenbach Canadian Limited. The patented method is limited to a thin porous material and wherein such material is passed through a drying chamber. It is obvious the entire material will be elevated in temperature because of being a thin porous material and because of being subjected to an enclosed heated chamber. Also because of using a drying chamber the process is highly energy intensive.

In many industrial processes where virtually instantaneous water content measurements are desired or required, it is common to measure an electrical property of the substance where a relationship between the electrical property and moisture content of the substance can be established. Moisture values estimated from electrical properties such as resistance, conductivity and capacitance are acceptably accurate, for the most part, when the materials on which measurements are being made are closely similar. However, it has been found that components of biological nature in particular, other than water, affect these electrical properties.

These components are primarily dissolved constituents and, as they vary in concentration and in relative proportions, the relationship between electrical properties and moisture values changes. Thus, these "instantaneous" types of measurement suffer from increasing inaccuracy, depending upon factors such as the nature of the biological material, its geographic origin, the climatic conditions under which it has developed and others.

For example, in the lumber industry electrical resistance meters are in common use for measuring moisture content. Notwithstanding that the meters have different calibrations for different wood species and corrections are applied for temperature differences, instances where actual values differ substantially from values predicted on the basis of electrical resistance measurement occur constantly. For unexplained reasons (since logs are not an annual crop), the relationship between electrical resistance values and actual moisture content of the lumber also appears to change with time, and must be re-evaluated periodically.

Another major shortcoming of these electrical techniques is that they require direct contact between the substance whose moisture content is being evaluated, such as wood, and the electrical device. For a resistance meter the pins, between which the resistance is measured, must be driven into the wood. This has obvious limitations for the on-line measurement of moisture values.

Another major shortcoming of the electrical techniques is their inability to measure what is called "free" water. In wood, electrical resistance increases with increasing water content up to about 30%, approaching the inherent value of water. Above this level, where the wood fibres are saturated with water, higher moisture levels cause no change in electrical resistance, and a resistance meter is effectively useless. Moisture levels in excess of 30% are common in unseasoned lumber, particularly for certain species. Radiofrequency methods of measuring high moisture content levels have been attempted, but as before, its accuracy has been found to be low. Under these circumstances, only oven drying techniques are accurate for obtaining meaningful high moisture measurements. The drawback of oven drying however is that it is energy intensive as the entire substance to be checked for moisture content is elevated in temperature.

SUMMARY OF INVENTION

In accordance with this invention, a process technique has been devised and apparatus for carrying out the same which is capable of rapidly and repeatedly enabling one to measure in acceptably accurate or "approximate" terms the moisture content of a substance without undue regard to dissolved constituents as above discussed or "free" water which give rise to erroneous moisture content ratings. Further, in practising the process of this invention, direct contact with the substance whose moisture content is to be measured or monitored can be avoided. The present invention also avoids the requirements of heating the entire substance as is the case with known heating techniques for measuring moisture content.

The process techniques and apparatus of this invention is derived from the fact that a relationship in the moisture content of a substance exists, in inverse proportion, to the rise in surface temperature of a substance subjected to heat. Surprisingly, what has been found is that the entire substance need not be elevated in temperature by being subjected to heat but instead only a surface portion thereof can be heated without sacrificing to any substantial degree the accuracy in the determining the moisture content.

The concept employed in realizing our invention for measuring moisture in a substance such as wood, is based on the mass of substance and water present, the specific heat of these two materials; specific heat being the quantity of heat required to increase the temperature of a unit mass of the substance by one degree—expressed in applicable units, and the heat of evaporation for water.

The concept is also based on the fact that, in the case of wood, for different species of wood, wood of different geographical origins, and wood subject to substantial climatic variations, the specific heat varies little, if at all, and can be considered to be constant. Further, the cooling effect from the heat of evaporation is believed to play an important role in controlling temperature rise.

Based on these factors, and in context of wood products and substances such as chips, wafers, sawdust and hogfuel, heat is applied to a fixed mass of wood (dry weight) containing an unknown mass of water, under adiabatic (perfectly insulated, i.e., no heat loss) conditions, one finds the rise in temperature to be inversely proportional to the unknown mass of water, as follows:

Specific heat of wood $= S_w$
Specific heat of water $= 1$ (by definition)
Known mass of wood $= W_o$
Unknown mass of water $= W_a$
Initial temperature $= T_i$
Final temperature $= T_f$
Heat of evaporation $= H_e$
quantity of heat applied $= Q$
Then $$Q = (T_f - T_i)[S_w \cdot W_o + 1 \cdot W_a] + W_a H_e$$

and $$T_f = \frac{Q + (S_w W_o + W_a) T_i - W_a H_e}{S_w W_o + W_a}$$

Thus the final temperature is governed by the above equation.

Based on the foregoing, there is an inverse relationship of temperature rise of the substance to its moisture content. We have surprisingly found that this holds true to acceptably accurate (referred to herein as "approximate") moisture content determinations regardless of wood thickness where the rise in temperature of the substance is measured at a selected surface area of the substance wherein such surface area only has been subjected or exposed to a predetermined intensity of heat for a selected period of time.

In accordance with one preferred method of this invention, therefore, the approximate moisture content of a substance can be determined by subjecting a surface area of the substance to a predetermined intensity of radiant energy for a selected period of time and thereafter measuring the rise in surface temperature of such surface area. It has been found that the rise in surface temperature is inversely proportional to the moisture content of the substance proximate the surface area in question, and from this moisture content can be determined simply by the measured rise in surface temperature; a high reading signifying a low moisture content and vice versa.

In situations where a surface length or endless surface lengths of a substance is to have its moisture content measured at intervals or continuously along the length, if the substance subjected to moisture content monitoring is of a constant temperature, then only the final temperature registrations need be read as being indicative of its moisture content. However, where the surface temperature of the surface length varies, or variations in initial temperatures between successive pieces of the same or similar substances are encountered, the rise in temperature can be measured by subtracting the initial surface temperature from the final surface temperature which is obtained following the application of heat.

In accordance with a further feature of the process, where a table has been prepared in advance for a known substance which sets forth, for a predetermined intensity of heat for a selected period of time, the relative relationship of rise in surface temperature to the approximate moisture content, readings obtained in the form of temperature rise can be readily converted to moisture content.

From the foregoing, it will be apparent that where the nature of the substance is known and temperature rise data as above described is available, moisture content readings can be rapidly determined.

The process of this invention also admits, however, to continuous determinations of relative variations in the approximate moisture content of a substance along a surface length of same or between successive separate pieces of the same substance. This latter attribute has particular appeal in the manufacture of lumber and plywood, as, for example, kiln-dried lumber normally must contain less than 19% moisture. Since the process of the invention facilitates the rapid approximate moisture content determination for individual pieces of lumber, lumber pieces can be graded and separated according to moisture content or moisture class which would then serve to predetermine the drying times for each of the different classes to produce a product containing less than 19% moisture. The ability to classify green lumber hitherto has not been possible or practical on a commercial scale.

It is well known that present adhesive formulations used in bonding individual veneers together to form a plywood have a limited moisture tolerance with the preferred range being between 3 and 6%. This can be accomplished in accordance with our novel process if drying times of individual sheets, or sorted groups thereof, are adjusted to conform to actual moisture. As in the case of green lumber, present attempts to do so are considered unsatisfactory resulting in poor product quality.

BRIEF DESCRIPTION OF THE DRAWINGS

In the accompanying drawings which illustrate data obtained in carrying out the process of this invention and one exemplary apparatus used in measuring moisture content in accordance with this invention:

FIG. 3 is a similar graph to that of FIG. 2 for the same types of veneers and spruce lumber but where different time limitations for the quality of heat applied is employed as described in Example 2 below;

FIG. 4 is a temperature profile curve that plots different surface temperature readings obtained at different locations along a veneer length as discussed in Example 3 below;

FIG. 7 illustrates the correlation between averaged surface temperature readings and their corresponding moisture content.

DESCRIPTION OF PREFERRED EMBODIMENTS

An apparatus capable of being used in the determination of the approximate moisture content of a substance by measuring a rise in a surface temperature of said substance as contemplated by our invention can comprise means for supporting the substance, heat and time means for applying a predetermined intensity of heat for a selected period of time to a surface area along a surface length of the substance, and temperature measuring means for determining the rise in the surface temperature at the surface area following the application of heat.

Where the substance or substances whose moisture content is to be measured are of the same initial temperature, the temperature measuring means need only be a temperature detection means which records the surface temperature of the surface area immediately following the application of heat. If, however, the initial surface temperature of the surface area to be heated varies along the length of the substance or varies between different pieces of the same substance, a further temperature detection means can be included for measuring this surface temperature prior to subjecting same to heat.

It will also be recognized that where continuous moisture content reading along the length of a substance is desired or required, the substance can be caused to move relative to the heat at a selected rate of travel and the temperature measuring means, or vice versa.

Figure 1:
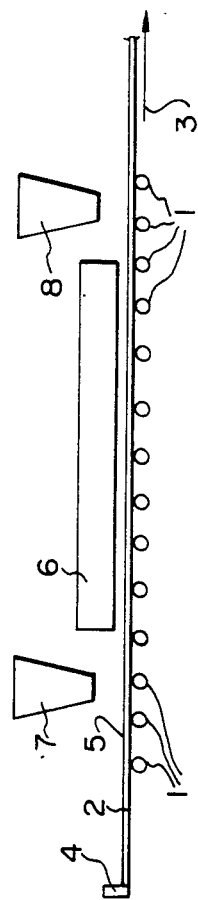
FIG. 1 is a schematic side view of one form of apparatus capable of intermittently or continuously measuring the rise in surface temperature on or along a surface length of a substance, such as wood, whose moisture content is to be determined.

With particular reference to FIG. 1, which illustrates in schematic form one apparatus suitable for use in carrying out the process of this invention, the means for supporting the substance is generally indicated by a series of conveyor rollers 1. The substance, in this case being a ⅛ inch wood veneer, 2, rests on rollers 1 and is permitted to move thereover in the direction of arrow 3 by virtue of feed means 4 which abuts the trailing edge of veneer 2.

Stationed above rollers 1 and veneer 2 and hence opposed a surface length 5 of veneer 2 is heat source 6 which is capable of delivering a preselected amount of heat to the wood surface 5.

Relative to the direction of movement (arrow 3) of veneer 2, heat sensor 7 is located upstream of heat source 6 whilst heat sensor 8 is located downstream of this heat source.

In the apparatus embodiment illustrated, conveyor 4 causes veneer 2 to move past sensors 7 and 8 and heat source 6 at a relative fixed speed thereto in a manner well known in the art. Because veneer 2 moves past heat source 6 at a constant rate of speed and because heat source 6 delivers a constant source of heat, the entire surface length 5 of veneer 2 is exposed to a uniform quantity of heat during its traverse. Further, immediately upstream of heat source 6, sensor 7 measures the initial surface temperature 5 prior to heat exposure whilst sensor 8 measures the final surface temperature immediately following heat exposure. The temperature difference, as above discussed, is related to the moisture content of wood veneer 2.

If, however, the initial temperature of substances whose moisture content is to be measured is constant, the initial surface temperature can be disregarded as a direct correlation between rise in surface temperature and moisture contact exists. For example, where successive veneers whose moisture contents are to be determined are of the same initial temperature, relative variations between each succeeding veneer section can readily be determined and compared directly from sensor 8.

Preferably, each of heat sensors 7 and 8 are infra-red heat sensors having a response time of 0.1 second. Heat source 6 can be a high energy point source such as an infra-red laser or one that acts over a wider area such as one or more infra-red heaters or a single platen. It will also be apparent where faster line speeds are used, a more intense heat source or more sensitive heat sensor may be necessary.

In the following examples, after final surface temperature measurements were recorded, the actual moisture content correlated thereagainst was obtained employing the above discussed oven dry method.

EXAMPLE 1

Figure 2:
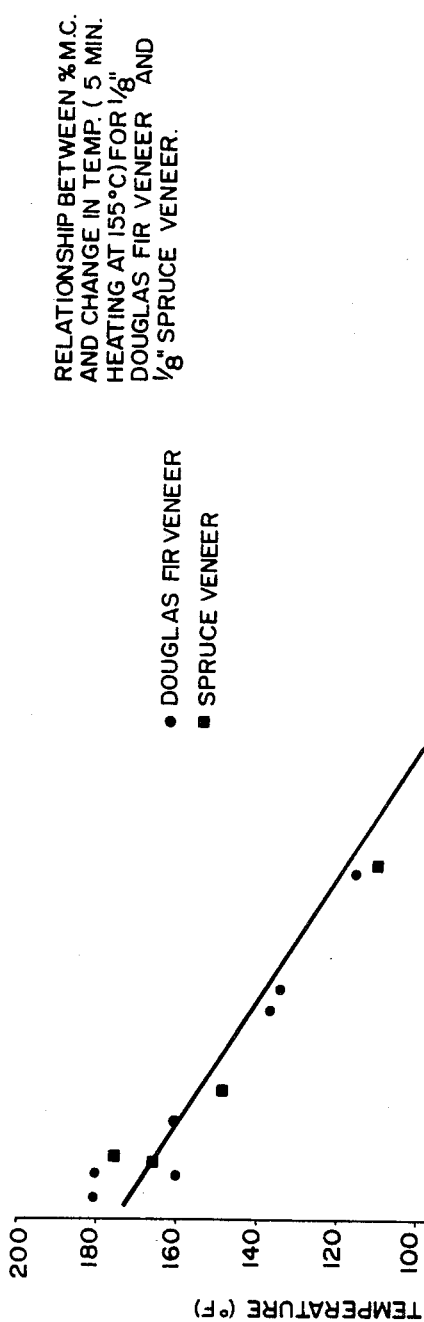
FIG. 2 is a graph plotting the percentage moisture content against change in surface temperature readings for veneers as described in Example 1 below.

Pieces of ⅛ inch Douglas fir and spruce veneer of different moisture contents were placed in a convection oven at 155 degrees Celcius for 5 minutes each. The surface temperature was then determined with a infra-red sensor with the resulting data obtained plotted as set forth in FIG. 2. A close relationship between the surface temperature of the veneer after 5 minutes of heating and its initial moisture content is self evident. Within the range of 10-80% moisture contents which is the moisture level range of interest in the manufacture and service life of wood products, it is evident that moisture content from a measurement of the rise in surface temperature can be predicted with reasonable accuracy.

It was also determined that an important aspect of the heating conditions is that the exposure to heat be sufficiently short such that only the surface of the wood respond to the input of heat. On this basis, the surface depths of the wood which respond to heat are a function of the heating conditions and are constant, as long as the heating conditions are held constant. Since only the surface of the wood is heated it is now possible with the present invention to measure, for example, moisture contents of pieces of wood of assorted thickness, shapes and sizes, utilizing the same test conditions.

EXAMPLE 2

In this example, two by four inch spruce lumber, ⅛ inch Douglas fir, and ⅛ inch spruce veneer specimens were each subjected to a heat input consisting of placing the wood pieces on a conventional solid-surface heating element for five seconds. The surface temperature of each of the wood pieces were then determined with an infra-red sensor and the results plotted in FIG. 3. Again, the results show a good relationship, indicating maximum accuracy for predicting initial moisture contents from surface temperatures of the wood, over the moisture range of 10–80%. It was also found that substantial variations in the size and shape of the wood pieces, and difference in species between the Douglas fir and spruce veneers, occasioned no more than minimal differences. The results indicate that the invention can be applied to wood of different shapes and sizes, and different species.

EXAMPLE 3

Pieces of ⅛ inch thick unseasoned spruce sap veneer, four by four feet in dimension, of different moisture content, were conveyed underneath two 2200 watt infrared heaters lined one directly behind the other each having a heating element 21.5 inches in length at a line speed of 43 feet per minute. The apparatus used in this example was similar to that illustrated in FIG. 1 with the exception that heat sensor 7 which measures the initial temperature was not necessary since all the veneershad an initial temperature of 70° F.

The distance between the wood surface and the heater was 0.75 inch. Heat sensor 8 measured the final temperature immediately after it passed the infrared heaters and the temperature profile was recorded on a strip chart recorder for each veneer. The temperature profile shown in FIG. 4 is representative, and gives a good indication of the variations in moisture content within a single veneer sheet along its length.

Figure 5:
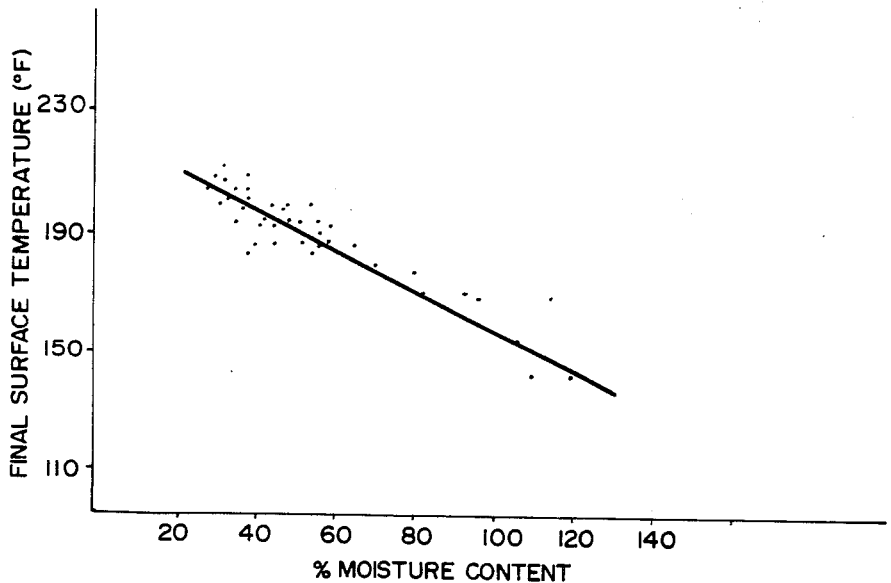
FIG. 5 is a graph wherein the surface temperature readings like those obtained in FIG. 4 are plotted against the percentage moisture content; to illustrate the correlation therebetween.

The temperature vs percentage moisture content results shown in FIG. 5 for the spruce sap veneers show a good correlation between the surface temperature readings and the moisture content readings of the veneers, whose moisture content was found to range from 30 to 130%.

EXAMPLE 4

Using the same apparatus described in Example 3, a number of two by six inch unseasoned hemlock-fir lumber 4 feet in length were conveyed under the infrared heaters at a line speed of 30 feet per minute such that the width portion passed under the heaters. Each length of lumber was positioned at right angles to the feed or line direction so that it could be passed under the heat source at four different locations therealong. Only the final temperature of the wood was measured since the initial temperature of the wood was constant at 70° F. Again, the distance between the wood surface and the heaters was 0.75 inch.

Figure 6:
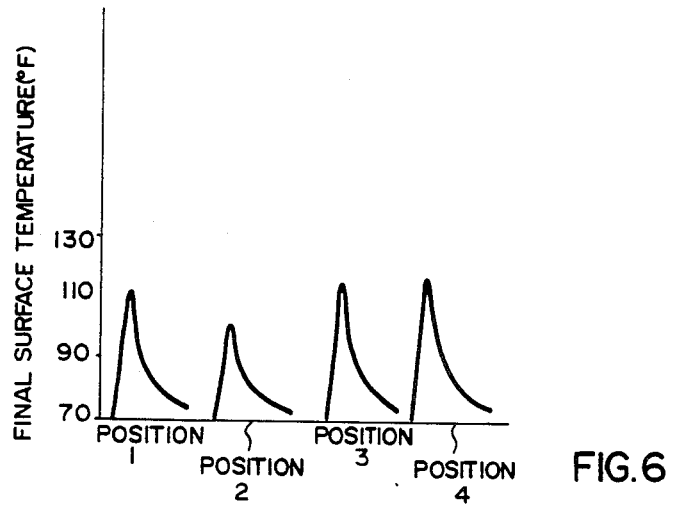
FIG. 6 illustrates in graph form final temperature readings obtained at four selected locations along a length of wood as discussed in Example 4.

The four surface temperature readings obtained for each piece of lumber were recorded on a strip chart, with one of the readings so obtained being illustrated in FIG. 6. Thereafter, each set of readings for each piece of lumber was averaged, with the averages so obtained plotted against the actual moisture content of each piece as determined by the oven dry methods, as seen in FIG. 7. As will be seen, a good and reproducible correlation exists between the average final temperature and moisture content of each piece over the range from 40 to 200%.

While we have principally disclosed our novel process and apparatus in context of measuring the moisture content of wood, it will be recognized that it can also be practised as a means for determining the moisture content of other substances such, as, for example, chips, wafers, sawdust and hogfuel.

We claim:

1. A method for use in rapidly determining the approximate moisture content of a piece of natural wood regardless of the thickness thereof and having an initial temperature, comprising:
    (a) directing radiant energy of predetermined intensity toward a selected area on one surface only of said wood piece to subject said surface to a predetermined quantity of energy for a selected period of time without appreciably changing the temperature of the wood piece below said surface;
    (b) measuring the temperature indicated by radiation from said selected area immediately following the application of said energy; and
    (c) comparing said measured temperature with said initial temperature, said temperature differences providing means to approximate the moisture content throughout said wood piece proximate said surface area on the basis that said rise in temperature is inversely proportional to said approximate moisture content.

2. The method as claimed in claim 1, wherein the initial temperature of said surface is first determined prior to subjecting said surface to radiant energy, and a rise in temperature is measured by subtracting said initial surface temperature from the temperature of said surface area measured immediately following the application of radiant energy.

3. The method as claimed in claim 1, wherein the approximate moisture content is determined by comparing a rise in temperature with a predetermined table relating to said wood piece and which sets forth, for said radiant energy of predetermined intensity and for selected period of time, the relative relationship of said rise in temperature to said approximate moisture content.

4. The method as claimed in claim 2, wherein said approximate moisture content is determined by comparing a rise in temperature with a predetermined table relating to said wood piece and which sets forth, for said radiant energy of predetermined intensity and for said selected period of time, the relative relationship of said rise in temperature to said approximate moisture content.

5. A method of determining relative variations in the approximate moisture content of a piece of natural wood regardless of the thickness of the wood at different locations therealong, comprising:
    (a) subjecting each one of a plurality of preselected surface areas along one surface only of a surface length of said wood piece to a same predetermined intensity of radiant energy for a same selected period of time without appreciably changing the temperature of the wood piece below said surface;
    (b) measuring the rise in surface temperature of each of said surface areas subjected to radiant energy; and
    (c) comparing the rise in surface temperature measurements so obtained for each said surface area on the basis that each measured rise in temperature for a given surface area is inversely proportional to the approximate moisture content throughout said wood piece adjacent said given surface area.

6. The method as claimed in claim 5, wherein the initial surface temperature of each of said surface areas prior to the application of heat is the same.

7. The method as claimed in claim 5, wherein said temperature rise for each said surface area is based upon the initial surface temperature of said surface area prior to the application of radiant energy and the final surface temperature of said surface area following the application of heat.

8. The method as claimed in claim 5, wherein for each of said surface areas, steps (a), (b) and (c) as set forth in claim 5 are carried out simultaneously.

9. The method as claimed in claim 5, wherein the rise in surface temperature for each of said surface areas is measured for each said surface area sequentially along said surface length of said wood piece.

10. The method as claimed in claim 1, wherein said wood piece is selected from a group consisting of solid wood, pieces of wood of varying shapes, sizes and thickness, wood chips and wood wafers.

11. The method as claimed in claim 5, wherein said wood piece is selected from a group consisting of solid wood, pieces of wood of varying shapes, sizes and thickness, wood chips and wood wafers.

12. The method as claimed in claim 5, wherein said surface length of said substance moves at a predetermined fixed speed relative to radiant energy source means and temperature measuring means for measuring said rise in said surface temperature.

13. A method of rapidly determining relative variations in the approximate moisture content between individual pieces of wood regardless of the thickness of the wood comprising subjecting each of said pieces on one surface only and at a selected surface area thereon to a same predetermined intensity of radiant energy for a same selected period of time without appreciably changing the temperature of each piece below said selected area, measuring the rise in temperature of said selected surface area and determining the moisture content of said pieces on the basis that said rise in temperature is inversely proportional to the moisture content of said piece.

14. The method as claimed in claim 13, wherein the initial temperature of said selected area of each said piece prior to same being subjected to radiant energy is the same.

15. The method as claimed in claim 13, wherein said temperature rise for each said surface area of each said piece is based upon the initial surface temperature of said surface area prior to same being subjected to radiant energy and the final surface temperature of the same said surface area following the application of radiant energy.

16. The method as claimed in claim 13, wherein said pieces are solid wood pieces.

17. The method as claimed in claim 13 wherein each said piece moves at a same constant speed firstly past a radiant energy source and secondly past temperature measuring means for measuring a rise in temperature.

* * * * *